(12) United States Patent
Murphy et al.

(10) Patent No.: US 9,552,629 B2
(45) Date of Patent: Jan. 24, 2017

(54) MEDICAL THERMAL IMAGE PROCESSING FOR SUBCUTANEOUS DETECTION OF VEINS, BONES AND THE LIKE

(71) Applicant: BAE Systems Information and Electronics Systems Integration, Inc., Nashua, NH (US)

(72) Inventors: Robert H. Murphy, Lancaster, MA (US); Paul J. Ilardi, Burlington, MA (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 0 days.

(21) Appl. No.: 14/655,070

(22) PCT Filed: Oct. 16, 2014

(86) PCT No.: PCT/US2014/060897
§ 371 (c)(1),
(2) Date: Jun. 24, 2015

(87) PCT Pub. No.: WO2015/061128
PCT Pub. Date: Apr. 30, 2015

(65) Prior Publication Data
US 2015/0324956 A1 Nov. 12, 2015

Related U.S. Application Data

(60) Provisional application No. 61/961,745, filed on Oct. 21, 2013.

(51) Int. Cl.
*G06K 9/40* (2006.01)
*G06T 5/00* (2006.01)
(Continued)

(52) U.S. Cl.
CPC ............... *G06T 5/002* (2013.01); *A61B 5/015* (2013.01); *G01J 5/026* (2013.01); *G06T 5/009* (2013.01); *H04N 5/217* (2013.01); *H04N 5/23229* (2013.01); *H04N 5/33* (2013.01); *H04N 5/357* (2013.01); *G01J 2005/0077* (2013.01); *G06T 2207/10048* (2013.01);
(Continued)

(58) Field of Classification Search
CPC ........... G06T 5/002; G06T 2207/10048; G06T 2207/20182; G06T 2207/20221; G06T 2207/20208; G06T 5/50; H04N 5/357; G06K 9/0051; A61B 5/015; G01J 2005/0077
USPC .................................................. 382/163, 175
See application file for complete search history.

(56) References Cited

U.S. PATENT DOCUMENTS

5,400,161 A * 3/1995 Lambert, Jr. ...... G02B 26/0816
250/208.1
7,173,245 B2 * 2/2007 Shakouri ................... G01J 5/00
250/339.1
(Continued)

*Primary Examiner* — Kanjibhai Patel
(74) *Attorney, Agent, or Firm* — Sand & Sebolt, LPA; Daniel J. Long (57) ABSTRACT

Medical thermal image processing for vein or other subsurface element detection and related methods is provided. A method for thermal image processing to enhance thermal scene information includes taking an output of an infrared camera and coupling the output to a spatial high pass filter. An output of the spatial high pass filter is then applied to a scene-based noise suppression module.

11 Claims, 5 Drawing Sheets

(51) Int. Cl.
　　　H04N 5/357　　　(2011.01)
　　　H04N 5/217　　　(2011.01)
　　　A61B 5/01　　　(2006.01)
　　　G01J 5/02　　　(2006.01)
　　　H04N 5/232　　　(2006.01)
　　　H04N 5/33　　　(2006.01)
　　　G01J 5/00　　　(2006.01)
(52) U.S. Cl.
　　　CPC ............. *G06T 2207/20182* (2013.01); *G06T 2207/20208* (2013.01); *G06T 2207/30101* (2013.01)

(56) References Cited

U.S. PATENT DOCUMENTS

| | | | |
|---|---|---|---|
| 7,558,436 B2 * | 7/2009 | Zuro | G06T 5/009 382/263 |
| 8,817,106 B2 * | 8/2014 | Richardson | H04N 5/23245 250/330 |
| 8,929,601 B2 * | 1/2015 | Caulfield | H04N 5/30 348/207.99 |
| 9,208,542 B2 * | 12/2015 | Hogasten | H04N 5/33 |
| 2008/0019608 A1 | 1/2008 | Zuro | |
| 2009/0175535 A1 | 7/2009 | Mattox | |
| 2011/0037835 A1 | 2/2011 | Morino et al. | |
| 2011/0262053 A1 | 10/2011 | Strandemar | |
| 2012/0321212 A1 | 12/2012 | Hgasten et al. | |
| 2014/0037225 A1 * | 2/2014 | Hogasten | G06T 5/50 382/260 |

* cited by examiner

MEDICAL THERMAL IMAGE PROCESSING FOR SUBCUTANEOUS DETECTION OF VEINS, BONES AND THE LIKE

CROSS REFERENCE TO RELATED APPLICATION

This application claims benefit of U.S. Provisional Application Ser. No. 61/961,745 entitled, "Medical Thermal Imaging Processing for Vein Detection" filed Oct. 21, 2013, the entire disclosure of which is incorporated herein by reference.

STATEMENT OF GOVERNMENT INTEREST

This invention was made with United States government support under contract number H9400304D0002/0086 awarded by the U.S. Air Force. The United States government has certain rights in this invention.

FIELD OF THE INVENTION

This invention relates to thermal imaging and more particularly to medical thermal energy imaging for detection of veins, bones, and the like.

BACKGROUND OF THE INVENTION

Various methods have been developed for the discernment of veins in the human body. However, improved means are needed for the rapid discernment of veins across various body types, skin colors, and topical features by persons of various medical experience levels. While infrared data systems have been utilized in the past to detect subsurface structures such as veins, bones, and other biologic materials, these systems have failed to provide sufficient resolution for the various body parts sought to be imaged.

In general, scene-based methods for low-frequency spatial noise removal and dynamic range enhancement involve removing slowly varying or low spatial frequency image content which adds little value to the visual perception of veins or other important objects found in thermal imagery in general and in medical thermal imaging in particular. These slowly varying image components may be due to anomalies within the thermal camera or they may be characteristics of the actual scene. They degrade the overall image quality and reduce the information accessible to the human observer by reducing the image dynamic range available for more valuable higher spatial frequency image content.

High spatial frequency image non-uniformity has an impact on the difficulty or ease with which veins and other important objects found in thermal imaging in general, and in medical thermal imagery in particularly, are perceived by a human observer. Noise and clutter also can have the same impact. For this reason the term spatial noise is often used to describe high spatial frequency image non-uniformity and is the term used herein.

Thus, a heretofore unaddressed need exists in the industry to address the aforementioned deficiencies and inadequacies.

SUMMARY OF THE INVENTION

Embodiments of the present disclosure can be viewed as providing a method for thermal image processing to enhance thermal scene information. In this regard, one embodiment of such a method, among others, can be broadly summarized by the following steps: taking an output of an infrared camera and coupling the output to a spatial high pass filter; and applying an output of the spatial high pass filter to a scene-based noise suppression module.

The present disclosure can also be viewed as providing a method of enhancing thermal imagery. In this regard, one embodiment of such a method, among others, can be broadly summarized by the following steps: applying at least one spatial bandpass filter to an image; and suppressing scene-based noise.

The present disclosure can also be viewed as providing a method of reducing fixed pattern or spatial noise from a frame sequence. In this regard, one embodiment of such a method, among others, can be broadly summarized by the following steps: subtracting a reference image from a frame sequence, wherein the reference image is created from a portion of the frame sequence.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

According to the present invention, medical thermal image processing for vein, bone, or other subsurface element detection, is accomplished by using a special band-pass and scene-based noise suppression filtering, pedestal subtraction, and thermal fusion image processing system. While prior art solutions apply a histogram-based, nonlinear transfer function to the image globally, or they may apply a variable linear gain and offset function locally, these solutions have not substantially enhanced the relevant thermal scene information revealed to the user.

On the other hand, in the subject invention, an infrared camera output is coupled to a spatial band-pass filter having a band limitation such that the high-pass cut-on spatial frequency is equivalent to a radius of 6 to 60 pixels. This configuration limits the input of spatial frequencies to the next step in the scene-based noise suppression system. In one embodiment, spatial noise removal is accomplished by measuring or estimating the spatial noise image contained within the original image followed by subtracting the spatial noise image from the original image. In another embodiment, the scene-based method is used to measure, estimate, or create, and then remove, spatial image noise from the real-time image sequence after an initial delay of a few seconds. After having removed spatial noise, one can consider pedestal subtraction.

Image dynamic range available to the human observer through a display is limited by many factors. Visual perception of a particular object in the scene is improved by utilizing as much of the available display dynamic range as is possible without degrading the dynamic range of other objects in the scene. Display dynamic range must thus be shared between many different scene components. To strike a proper balance, it is necessary to reduce the contrast of large and naturally high contrast scene elements prior to display in order to reserve display dynamic range for small but important scene elements that may be of low contrast in the scene.

Thermal fusion can also be used to emphasize subcutaneous objects. As to thermal fusion, thermal imagery can be viewed as having two types of scene information. The first type of scene information is the size and shape of the various objects in the scene and the second type of scene information is temperature. By combining both size/shape and temperature one can enhance various attributes of the subsurface objects so they can be readily visualized.

Further enhancements can be achieved by post processing. For example, in one embodiment the captured 16-bit raw data is post processed with suitable image processing algorithms to produce a number of long-wavelength infrared (LWIR) movies as well as the images appearing herein.

In the subject system, the scene-based noise suppression system has a low spatial frequency noise removal system operating with a spatial band-pass filter frequency equivalent to a radius greater than 60 pixels to 480 pixels. The combination of these spatial frequency filters increases the dynamic range and contrast for the objects of interest. The scene-based noise suppression system also has a high-frequency fixed pattern, a slowly varying pattern, or a spatial noise removal system for the removal of unwanted image artifacts which degrade the visual experience of trying to resolve a vein or other subsurface features such as a bone. The spatial band-pass filter in combination with the scene-based noise suppression provides a thermal image processing system that enhances and enables more efficient coupling to the human visual system of the observer of the thermal scene information.

After the thermal image processing, additional enhancement may be obtained through a pedestal subtraction system where a greater portion of the scene dynamic range is efficiently coupled to the observer through the display. Pedestal subtraction reduces the excess dynamic range of large naturally occurring high contrast scene elements thus enabling smaller, low contrast and important scene elements such as veins to occupy a larger portion of the display dynamic range than would be possible without pedestal subtraction.

Further visualization of the subsurface structure may be provided by a fusion of enhanced thermal elements with non-enhanced thermal elements so as to provide a combined thermal fusion image processing system which utilizes the shape of the subsurface element and its relative temperature in order to be able to distinguish the particular subsurface artifact or structure. In the thermal fusion image processing system, care is taken to keep all parts of the image out of saturation so that vein structure and bone structure can be easily viewed not only for its position and shape but also for its color, all of which correlates to its temperature.

Unsharp masking may also be utilized in which the unsharp masking technique utilizes an unusually large radius of 7 to 70 pixels to enhance a wide range of medium to high-spatial frequency features that make the subsurface structures more visible and distinguished from the low-frequency thermal background. The processing involved in rendering the image incorporates a real-time full-frame rate system which involves a scene-based method for low-frequency spatial noise removal and dynamic range enhancement in which slowly varying or low-frequency image elements are removed by a spatial band-pass filter that removes the low spatial frequency image components.

Secondly, the scene-based method for eliminating spatial or fixed pattern noise involves a method for eliminating high-frequency spatial or so-called fixed pattern noise, meaning noise and clutter removal, by removing a high spatial frequency filtered version of the image from the original image. This removal is done in one embodiment by measuring or estimating the spatial or fixed pattern noise within the image and subtracting it from the original image.

A specialized algorithm for removal of the spatial image involves first creating a frame stack "SBN stack" by applying a 3 to 12 pixel radius spatial high pass filter to the previous two or more frames. Secondly, and in parallel, a frame stack "SBN mask stack" is created by thresholding the 3 to 12 pixel radius variance of each of the previous two or more frames. The next step is to remove the residual scene content from each frame in the stack by applying the "SBN mask stack" as a mask to each frame in the "SBN stack". The result is "SBN masked stack." The next step is to create a spatial noise reference image "SBNref image" by computing the stack frame average of the masked stack. The final step is the removal of the spatial noise from each subsequent frame by subtracting the "SBNref image" from each subsequent frame.

After the scene-based method for noise removal, pedestal subtraction is utilized to preserve display dynamic range for small but important scene elements that may be of low contrast in the scene itself. This pedestal subtraction is done by reducing the contrast of large and naturally high contrast scene elements prior to display. The result is to preserve display high dynamic range for small but important scene elements that may be of low contrast.

After pedestal subtraction, thermal fusion is utilized to meld the size and shape of objects with their temperatures such that the combination of the two parameters heightens the visibility of the particular elements so that they may be visualized easily from the display.

In addition to the above enhancements for the display of thermal imaging, post processing in one embodiment captures 16 bit raw data, linearly stretches the 16-bit data of a single frame, and both provides a 16 frame moving average filtration and at the same time increases subject contrast so as to be able to pop out or make more visible the subcutaneous object required. Rather than utilizing thermal cameras which have minimal image processing built-in, namely just enough to be able to produce a linear level image or linear mapping of the thermal scene, in the subject invention details in the thermal scene required to be enhanced so as to be easily detectable are provided by thermal image processing systems. These systems utilize spatial band-pass and scene-based noise suppression filtering as well as pedestal subtraction, thermal fusion image processing and unsharp masking.

Figure 1A:
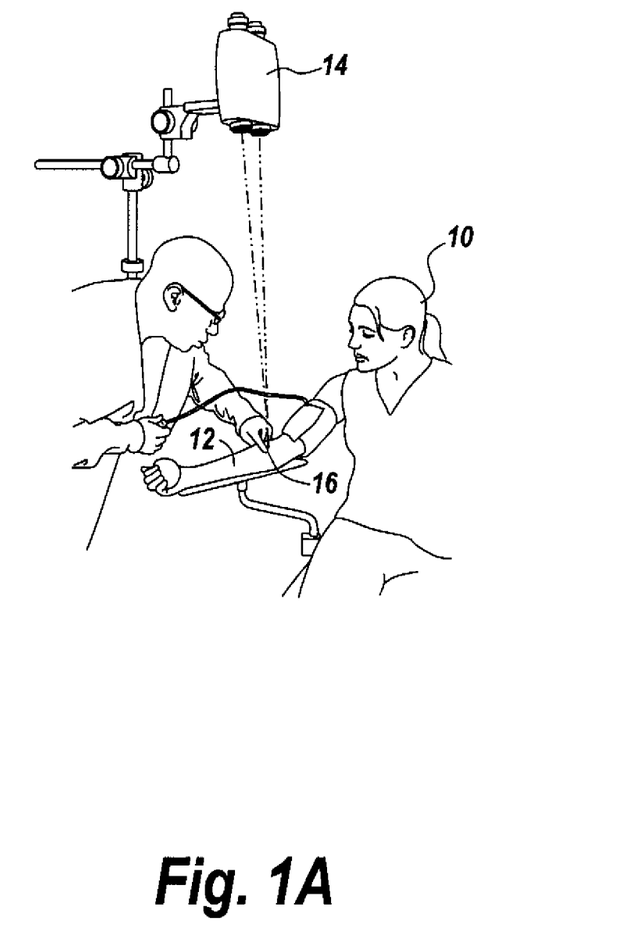
FIG. 1A is a diagrammatic illustration of the inspection of the arm of the patient utilizing an infrared imaging system, in accordance with a first exemplary embodiment of the present disclosure.

FIG. 1A is a diagrammatic illustration of the inspection of the arm of the patient utilizing an infrared imaging system, in accordance with a first exemplary embodiment of the present disclosure. In FIG. 1A, a patient 10 has an arm 12 that is being inspected by a binaural infrared camera 14 which is focused upon point 16 on the patient's arm. The purpose of the subject technique is to take the infrared camera images and to enhance the subsurface structure within the image, most importantly veins or bones within the patient.

Figure 1B:
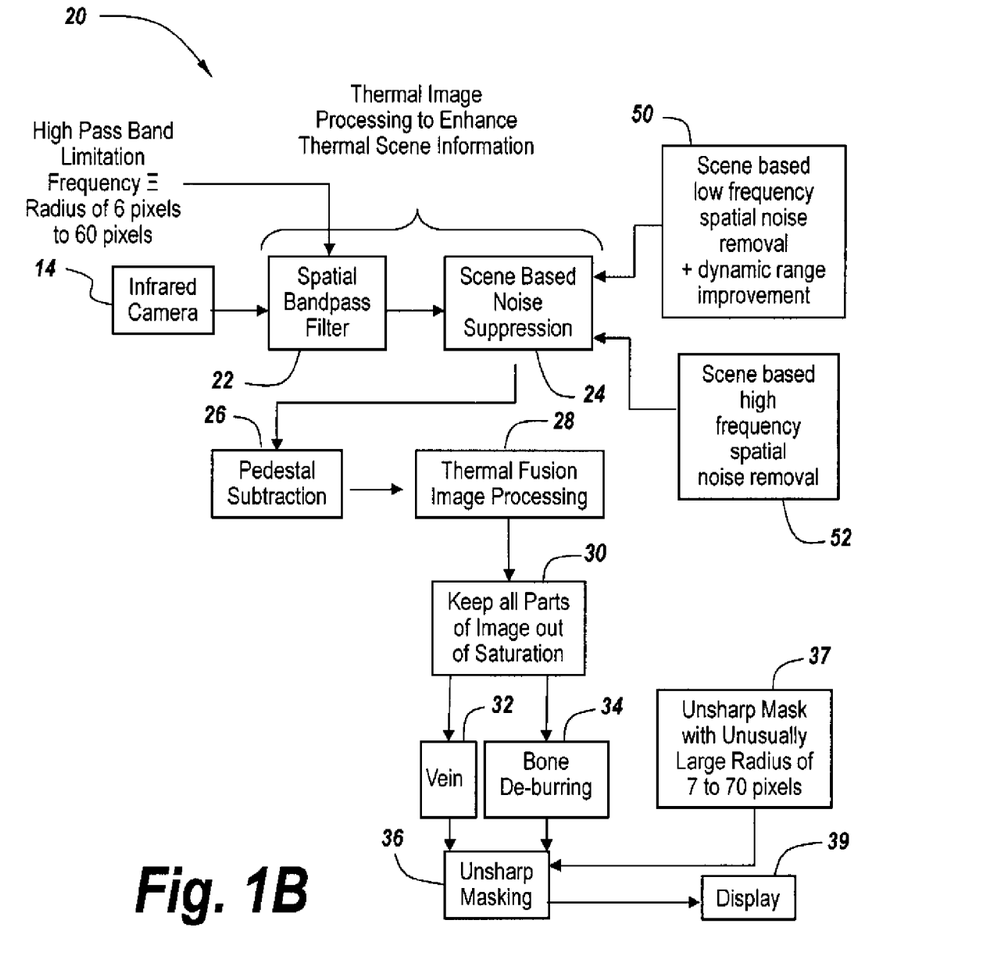
FIG. 1B is a flow schematic diagram of the infrared imaging system in which the infrared camera is coupled to a spatial band-pass filter, a scene-based noise suppression module, a pedestal subtraction unit and a thermal fusion image processing system, followed by unsharp masking to be able to exaggerate or enhance subsurface objects such as veins or bone burrs, in accordance with the first exemplary embodiment of the present disclosure.

FIG. 1B is a flow schematic diagram of the infrared imaging system in which the infrared camera 14 is coupled to a spatial band-pass filter, a scene-based noise suppression module, a pedestal subtraction unit and a thermal fusion image processing system, followed by unsharp masking to be able to exaggerate or enhance subsurface objects such as veins or bone burrs, in accordance with the first exemplary embodiment of the present disclosure. As is shown in FIG. 1B, the thermal image processing system 20 takes the output of an infrared camera 14 and couples it to a spatial band-pass filter 22 that is, in turn, coupled to a scene-based noise suppression unit 24. The output of the scene-based noise suppression unit 24 is coupled to a pedestal subtraction module 26. The pedestal subtraction unit 26 may be used to preserve as much of the available display dynamic range as possible by reducing contrast of large and naturally high contrast scene elements, thus to be able to visualize small low contrast scene elements.

The output of the pedestal subtraction module 26 is coupled to a thermal fusion image processing module 28. The output of thermal fusion image processing module 28 is controlled at saturation controller 30 to keep all parts of the image out of saturation, such that veins or bone de-burring structures are visible, as indicated by boxes 32 and 34. The resulting output of the thermal fusion image processing module 28 is passed through an unsharp masking module 36 to remove noncritical artifacts in the infrared camera output. Unsharp masking module 36 is under control of control unit 37 which restricts the unsharp masking to using an unusually large radius of 20 pixels. Thereafter, the results are displayed on a display 39.

The scene-based noise suppression module 24 may include two different types of noise suppression systems. The first type utilizes a low-frequency spatial noise removal system 50 in which spatial noise of a low-frequency nature is removed which simultaneously improves the dynamic range for those small indistinct subsurface elements of interest. The second type of system used by the scene-based noise suppression module 24 is a scene-based high-frequency spatial noise removal module 52 which removes high-frequency spatial noise.

Figure 2A:
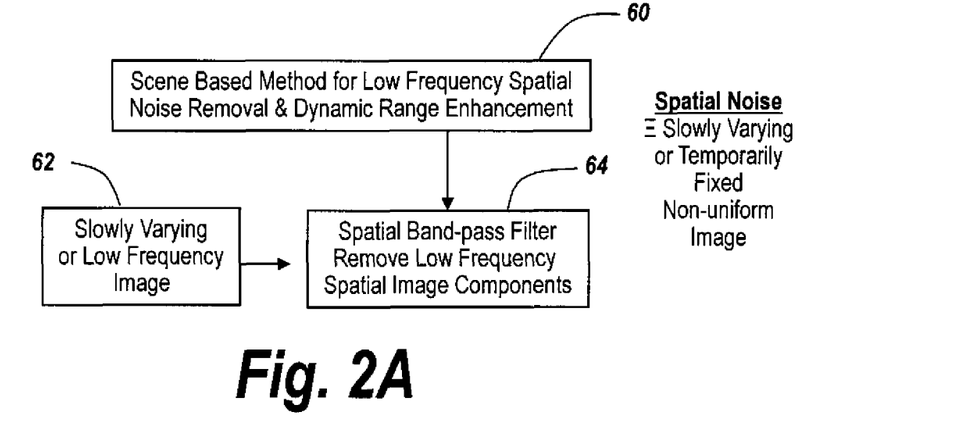
FIG. 2A is a diagrammatic illustration of real time full frame image processing for both low-frequency spatial noise removal and dynamic range enhancement, in accordance with the first exemplary embodiment of the present disclosure.

FIG. 2A is a diagrammatic illustration of real time full frame image processing for both low-frequency spatial noise removal and dynamic range enhancement, in accordance with the first exemplary embodiment of the present disclosure. FIG. 2A illustrates the basics of the real-time full-frame image processing available for scene-based noise suppression. As illustrated at block 60, the scene-based method for low-frequency spatial noise removal and dynamic range enhancement starts off with slowly varying or low-frequency images within block 62. The slowly varying or low-frequency images of block 62 may be applied to a spatial band-pass filter at block 64 to remove low-frequency spatial image components.

Figure 2B:
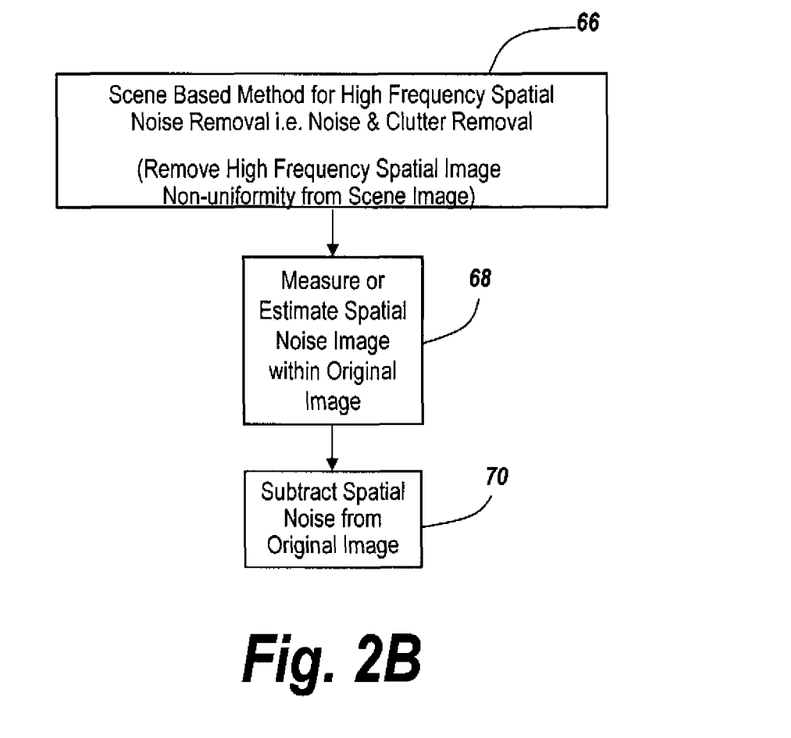
FIG. 2B is a diagrammatic illustration of real time full frame image processing for scene-based methods for high-frequency spatial noise removal including clutter, in accordance with the first exemplary embodiment of the present disclosure.

FIG. 2B is a diagrammatic illustration of real time full frame image processing for scene-based methods for high-frequency spatial noise removal including clutter, in accordance with the first exemplary embodiment of the present disclosure. As is shown, the method provides for removal of high-frequency spatial elements to permit noise removal and thus clutter as well. The method includes removal of high-frequency spatial image nonuniformity from the scene image at block 66. Next, at block 68, the spatial noise image within the original image is measured or estimated. At block 70, the spatial noise is then subtracted from the original image. In either FIG. 2A or FIG. 2B, spatial noise may refer to the slowly varying or temporally fixed nonuniform images within the scene.

Figure 3:
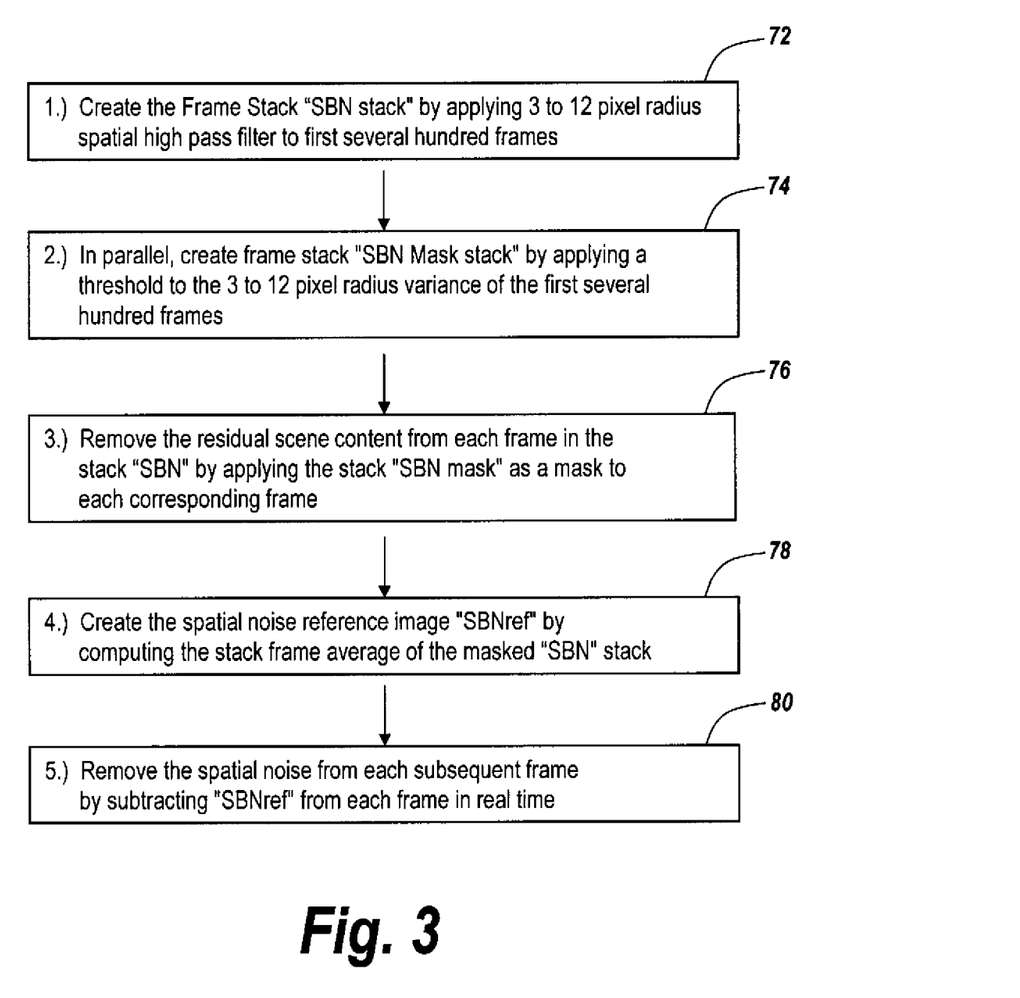
FIG. 3 is a flowchart showing method steps for removal of spatial noise, in accordance with the first exemplary embodiment of the present disclosure; and, FIG. 4 is a diagrammatic representation of the use of pedestal subtraction, thermal fusion and post processing to increase the contrast invisibility of small subsurface objects, in accordance with the first exemplary embodiment of the present disclosure.

FIG. 3 is a flowchart showing method steps for removal of spatial noise, in accordance with the first exemplary embodiment of the present disclosure. In order to remove spatial noise, the frame stack SBN stack is created by applying a 3 to 12 pixel radius spatial high pass filter to the first several hundred frames, as is shown at block 72. The frame stack SBN mask stack is then created, in parallel, by applying a threshold to the 3 to 12 pixel radius variance of the first several hundred frames, as is shown at block 74. The residual scene content from each frame in the stack SBN is removed by applying the stack SBN mask as a mask to each corresponding frame, as is shown at block 76. The spatial noise reference image SBNref is then created by computing the stack frame average of the masked SBN stack, as is shown at block 78. Spatial noise is then removed from each subsequent frame by subtracting the "SBNref image" from each frame in real time, as is shown at block 80.

Figure 4:
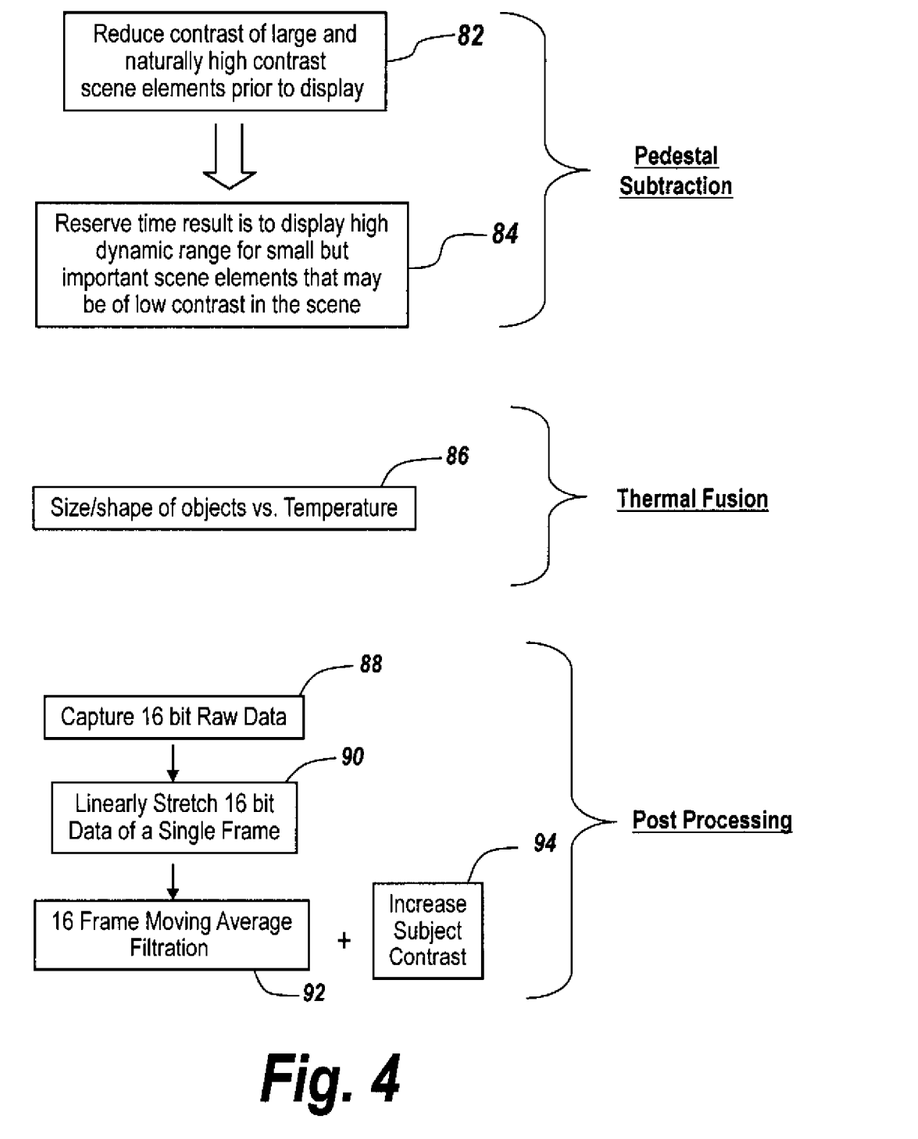

Removal of scene-based noise as well as providing a spatial band-pass filter improves the enhancement of the subsurface objects within the human anatomy. However, further enhancements may be obtained by utilizing a technique called pedestal subtraction. FIG. 4 is a diagrammatic representation of the use of pedestal subtraction, thermal fusion and post processing to increase the contrast invisibility of small subsurface objects, in accordance with the first exemplary embodiment of the present disclosure. As is seen in FIG. 4, pedestal subtraction provides for reserve time result to display high dynamic range for small but important scene elements that may be of low contrast in the scene. Pedestal subtraction may include reducing contrast of large and naturally high contrast scene elements prior to display, as is shown at block 82. Reducing contrast may then allow for reserving a time result to display the high dynamic range for the small but important scene elements that may be of low contrast, as is shown at block 84.

Next, using a process of thermal fusion, two different types of information may be taken into account in order to display the subsurface object, as is shown at block 86. The first type is the size or shape of the object as well as its location and the second type is its temperature. By displaying these two simultaneously one can enhance the features that are sought after especially small subsurface objects that are not generally high contrast can be seen.

Subsequently, at post processing, further enhancements can be obtained. As is shown at block 88, 16 bit raw data may be captured. Thereafter, as shown at block 90, the 16 bit data is linearly stretched corresponding to the stretching of a 16-bit data of a single frame. Next, a 16 frame moving average filtration may be used simultaneously with a system for increasing the contrast of the object sought after, as is shown at block 92 and block 94, respectively.

What is therefore shown is a system for enhancing thermal imaging to be able to visualize and enhance subsurface objects within a human or mammalian context in which thermal imaging cameras can be used with enhanced techniques to be able to make visible various small and non-contrasted features that lie beneath the surface of the skin.

While the present invention has been described in connection with the preferred embodiments of the various Figures, it is to be understood that other similar embodiments may be used or modifications or additions may be made to the described embodiment for performing the same function of this present invention without deviating therefrom. Therefore the present invention should not be limited to any single embodiment, but rather construed in breadth and scope in accordance with the recitation of the appended claims.

What is claimed is:

1. A method for thermal image processing to enhance thermal scene information, comprising the steps of:
    taking an output of an infrared camera and coupling the output to a spatial high-pass bandpass filter; and,
    applying an output of the spatial high-pass bandpass filter to a scene-based noise suppression module processor,
    wherein the scene-based noise suppression processor further comprises at least one of:
    removing scene-based low-frequency spatial noise and dynamic range improvement; and
    removing scene-based high-frequency spatial noise.

2. The method of claim 1, further comprising coupling an output of the scene-based noise suppression module processor to a pedestal subtraction module.

3. The method of claim 2, wherein the pedestal subtraction module reduces a contrast of large and naturally high contrast scene elements prior to display, whereby a high dynamic range is displayed for small scene elements that are of low contrast.

4. The method of claim 1, further comprising taking at least one of a slowly varying and a low-frequency image and spatially filtering the image to remove low-frequency spatial image compliments using a real-time full-frame rate system, wherein the real-time full-frame rate system functions as a scene-based method for low-frequency spatial noise removal and dynamic range enhancement.

5. The method of claim 4, wherein the real-time full-frame rate system includes a scene-based method for high-frequency spatial noise removal including noise and clutter removal by removing high-frequency spatial image non-uniformity from scene images.

6. The method of claim 5, wherein the scene-based method for high-frequency spatial noise removal further comprises at least one of measuring and estimating spatial noise within an original image, and further comprises subtracting the at least one of measured and estimated spatial noise from the original image.

7. The method of claim 6, wherein the method for removing spatial noise further comprises:
    creating a frame stack by applying a pixel radius of a predetermined number of pixels to provide a high pass filter to a predetermined number of frames;
    in parallel, creating a frame stack mask by applying a threshold of a predetermined pixel radius variance to a first of said frames; creating a spatial noise reference image by computing a stack frame average of a masked stack; and,
    removing a spatial noise from each subsequent frame by subtracting the spatial noise reference image from each of said frames.

8. The method of claim 1, further comprising applying a thermal fusion image processing to an output of the scene-based noise suppression module processor.

9. The method of claim 1, further comprising applying thermal fusion image processing to an output of the pedestal subtraction module.

10. The method of claim 1, further comprising:
    coupling an output of the thermal fusion image processing to an unsharp masking optical element; and,
    displaying a result of the output of the unsharp masking element.

11. A method of enhancing thermal imagery comprising:
    applying at least one spatial bandpass filter to an image obtained from an infrared camera aimed at mammalian skin; and
    suppressing scene-based noise in a noise suppression module processor to visualize and enhance objects that lie below the skin surface,
    wherein suppressing scene-based noise further comprises at least one of:
    scene-based low-frequency spatial noise removal and dynamic range improvement; and
    scene-based high-frequency spatial noise removal.

* * * * *